United States Patent
Eriksen et al.

(10) Patent No.: US 6,759,353 B2
(45) Date of Patent: Jul. 6, 2004

(54) ABSORBING ARTICLE

(75) Inventors: Marianne Etlar Eriksen, Rønde (DK); Jeanette Almstrøm, Knebel (DK)

(73) Assignee: Panolana ApS, Knebel (DK)

(*) Notice: Subject to any disclaimer, the term of this patent is extended or adjusted under 35 U.S.C. 154(b) by 247 days.

(21) Appl. No.: 10/126,575

(22) Filed: Apr. 22, 2002

(65) Prior Publication Data

US 2003/0119407 A1 Jun. 26, 2003

(30) Foreign Application Priority Data

Dec. 21, 2001 (DK) .......................................... 2001 01940

(51) Int. Cl.$^7$ ................................................ A61F 31/20
(52) U.S. Cl. ...................... 442/85; 442/369; 442/381; 442/383; 442/416; 604/358; 604/378; 604/385.01
(58) Field of Search ...................... 442/85, 369, 381, 442/383, 416; 604/358, 378, 385.01

(56) References Cited

U.S. PATENT DOCUMENTS

| | | | |
|---|---|---|---|
| 4,737,582 A | * | 4/1988 | Goldman et al. .............. 536/2 |
| 5,506,277 A | * | 4/1996 | Griesbach, III ............ 521/84.1 |
| 5,759,569 A | * | 6/1998 | Hird et al. .................. 424/443 |
| 6,492,574 B1 | * | 12/2002 | Chen et al. ................. 604/378 |

* cited by examiner

Primary Examiner—Terrel Morris
Assistant Examiner—John J. Guarriello
(74) Attorney, Agent, or Firm—James Creighton Wray; Meera P. Narasimhan

(57) ABSTRACT

An absorbing article has a hydrophobic, liquid impermeable back side layer and a liquid permeable top layer together with an interposed hydrophilic core layer. The article is made so that at least the back side layer comprises hydrophobic vegetable fibers, preferably kapok fibers, and that the top lay can comprise wool fibers.

Such an article is advantageous since it may be used for keeping the user warm in situations where there is need for liquid absorption without the risk of unintended temperature elevation known from plastic products.

13 Claims, No Drawings

ABSORBING ARTICLE

This application claims the benefit of Danish Application No. PA 2001 01940 filed Dec. 21, 2001.

BACKGROUND OF THE INVENTION

The present invention concerns an absorbing article having a hydrophobic, liquid permeable top layer, a hydrophobic liquid impermeable back sheet and a hydrophilic core layer.

The invention particularly concerns absorbing articles that may be used as diapers for adults or children, as sanitary tissue or draw sheets for use in surgery and absorbing dressing by burns that presuppose sterile environment, or dressings for wounds produced by traumas or circulation related symptoms.

The absorbing articles have other applications where it is desirable to avoid exposure to cold or moisture for the person being in contact with the absorbing article, in situations where there is need for absorption of liquid.

Many examples of absorbing articles of the kind mentioned in the introduction are known. These usually are made with a combination of cellulose fibers in the core layer and plastic materials in the top layer and the back side layer. Also, there have been proposals of making absorbing articles where the top layer and the back side layer are made of modified cellulose.

Usually the core layer is made by a dry forming process, and this layer is subsequently placed between top layer and back side layer at the subsequent processes and/or in subsequent processing machines.

With the prior art product it is realized that a risk of temperature elevation may arise due the impermeable plastic materials. Furthermore, there is also the risk of moisture action of the body being in contact with the top layer. The temperature elevation may particularly be a problem for boys as there is a risk of sterility. The moisture accumulation also gives rise to skin irritation and hypersensitivity. Furthermore, there is a risk of allergy and complications due to skin contact with plastic materials.

SUMMARY OF THE INVENTION AND DETAILED DESCRIPTION OF THE PREFERRED EMBODIMENTS

It is the object of the present invention to provide an absorbing article, where these drawbacks are relieved, and which enables production of fibers allowing the skin to breathe while maintaining the body temperature of the person. Furthermore, it is an object to provide an absorbing article which can be made by a dry forming process.

According to the present invention, this is achieved with an absorbing article peculiar in that at least the back side sheet comprises hydrophobic vegetable fibers or animal fibers.

The vegetable fibers are preferably kapok fibers, and the animal fibers are preferably wool fibers.

It is also possible to use these hydrophobic vegetable fibers in every layer, and it is preferred also that at least the top layer comprises animal fibers.

The wool fibers are structured as the skin with different proteins, inter alia keratin, and therefore are not alien to the skin. The wool fibers are not static and act like skin tissue with calming effect.

The absorbing article may particularly be used where it is desirable to have an absorbing layer close to the body with a lower temperature than that of the body in order thereby to avoid heat loss which is also an energy loss. For small children who are growing rapidly, or for damaged skin or body parts, the temperature is analogous with an optimal blood circulation, implying the best conditions for growth and healing. It is possible to avoid temperature or moisture action on the person being in contact with the absorbing article in situations, where there is need for liquid absorption.

With such an absorbing article and due their structure, the vegetable fibers will allow the skin to breathe and at the same time keep the person warm without risk of becoming too hot. Thus there is risk that the temperature is elevated to such level that there is danger of damaging influence. If all three layers are made with the hydrophobic vegetable fibers a very advantageous product is achieved.

The top layer of the absorbing article may be made of a hydrophobic vegetable fiber only, or wool fibers only, or a combination of these fibers.

By using kapok fibers, or predominantly kapok fibers, there is achieved a distinctly hydrophobic layer, and the user will experience a total dryness on the body. In the top layer there will be a need for mechanical perforation in order thereby to provide possibility of passage of liquid. Such perforation may preferably occur by mechanical forming of holes through embossing. This may take place by using a calendar roller which is used immediately after the dry forming of the top layer.

The natural liquid passage through the fibers of the top layer, which are appear tangled up, will be insufficient to secure a rapid liquid passage through the layer.

By using the hydrophobic vegetable fibers, preferably kapok fibers in the top layer, decomposition of ammonia gases cannot occur, which is desirable in diaper products. The ammonia gasses in such an article can only be decomposed in the absorbing layer and in the back side layer, where in one or both layers there will be provided lanolin-containing wool as the greater or lesser part and mixed with the hydrophobic vegetable fibers.

The presence of lanolin is decisive in an absorbing article used for absorbing urine, and it is important that the lanolin occurs together with the vegetable fibers.

A top layer made of wool only is a possibility, though it is preferred that the top layer contains kapok fibers.

If the top layer is made from wool fibers, the layer is to be impregnated by spraying on lanolin, glycerine or other liquid barrier means, which is preferably applied in an aqueous solution. The wool may only by itself be hydrophobic in the outermost surface layer in the top layer facing the body. Hereby is achieved simultaneously a very beneficial and healing effect on wounds, making such absorbing articles advantageous for use in wound dressings.

When wool fibers and vegetable fibers are used in a mix ratio, an optimal hydrophobicity is achieved simultaneously with the possibility of decomposing the ammonia in the top layer.

It is possible to mix the fibers with consideration to the intended application of the article for medical use, diapers, sanitary tissue, or the like. A typical mixture for children will be 75% wool fibers and 25% kapok fibers, however, with the possibility of varying these conditions so that the wool fiber part may be between 50 and 85%, and the kapok fiber part be between 50 and 15%. For adult diapers, the typical mix ratio will be 50% wool fibers and 50% kapok fibers. This mix ratio may, however, vary from 25 to 50% wool fibers and from 75 to 50% kapok fibers. It is, however, possible to use a lesser part of kapok fibers if impregnation takes place as mentioned above.

In sanitary tissue, the mix ratio will typically be 25% wool fibers and 75% kapok fibers. It is, however, possible to vary this mix ratio so that the wool fiber part may be between 0 and 25%, and the share of kapok fibers may be between 100 and 75%. This is also the case for this product that the kapok fiber content may be less if impregnation is used.

In connection with the above mix ration, it is preferred primarily to use as large share of vegetable fibers, preferably kapok fibers, as possible, irrespectively whether this implies the need for mechanical perforation with the purpose of rapid passage of liquid through the top layer.

Kapok fibers are cheap vegetable fibers which are easily accessible in bushes and trees. The fibers require largely no preparation except for sifting and cleaning in order to remove seed. Then it is possible to use the fibers directly by a dry forming process. The combination of the hydrophobic properties of the kapok fibers, and a possibility of directly using these, largely without any preparation, in a dry forming process, makes the fibers particularly suited for use in making absorbing articles.

Even though it is preferred to use kapok fibers, it is possible to substitute these with fibers of flax and hemp which thus may be made hydrophobic also. Other vegetable fibers are also possible.

Usually, fibers with a length of a few millimeters, typically 3–5 mm, will be used. However, the vegetable fibers may have a length of up to 8 mm for special types of kapok.

When the absorbing article is to be used within the hospital sector, it is preferred to use the above mentioned glycerine impregnation of the fibers. Alternatively, the glycerine may be applied in thin layers. The glycerine is well suited for use in wound care and has healing effect and is simultaneously a natural product without any detrimental side effects. This implies that the user do not get any harmful side effects by using the absorbing article according to the invention.

The absorbing layer will preferably be made with absorbents in the form of vegetable starch, preferably potato flour. The absorbents will be fixed in the open structure formed by the vegetable fibers.

It is to be noted that potato flour is advantageous compared with artificial super absorbents as potato flour has a healing effect. Potato flour may usually not be used as it collapses at the initiation of liquid absorption. This means that only in the outermost part of the absorbents or particles there is possibility of using the absorbing ability. As the absorbents are kept separate in the matrix formed by the tangled vegetable fibers, the potato flour will be supported so that collapse does not occur. This means that the entire absorbing ability may be utilized.

As alternative to potato flour, vegetable starch may be used, e.g. From corn or rice.

Even though it is preferred to use potato flour, it is possible to produce the absorbing article according to the invention with super absorbents. This may be an advantage when the article is to be used as an incontinence diaper for adult person with great incontinence, or similar products with very great need for liquid absorption.

The absorbing layer may contain a share of cellulose fibers which in way known per se are used for absorption. Such cellulose fibers may be used alone or in combination with the absorbents.

The absorbing layer contains preferably hydrophobic fibers, e.g. fibers of flax or hemp which are cheaper than kapok fibers.

In the absorbing layer, it is also possible to use different types of fibers, for example curly fibers, a very absorbing type of cellulose fibers. Other pulped wood celluloses may also be used. A main property in the insulating layer is the use of hydrophobic fibers which enable retention of an open structure in order to avoid collapse, thereby attaining a better absorbing ability. At the same time, compared with prior art, it will be possible to save synthetic fibers and binders which are used for forming a lattice network keeping the core material open in traditional products where the core layer only contains cellulose fibers.

As mentioned, it will be possible to make the absorbing layer with a mixture of wool and kapok or other vegetable fibers in order to maintain the open structure in the core layer.

The core layer is usually made with gram weights depending on the intended application. For child diapers, a core layer with gram weights between 150 and 250 $g/m^2$ will thus be provided. For sanitary tissue, layers with gram weights between 30 and 70 $g/m^2$ will be provided. For adult diapers, layers with gram weights between 400 and 500 $g/m^2$ will be provided.

The liquid barrier back side layer will preferably be made of largely pure kapok fiber. It is possible to perform an impregnation of the other surface layer with liquid barrier agent, as for example lanolin or glycerine.

The back side layer will preferably be made with heat compacting in immediate association to a dry laying process.

In the back side layer, there may possibly be provided a small part of wool fibers. These wool fibers may preferably be impregnated. The wool fibers contribute to the ability of the absorbing article to maintain the temperature of the user and thereby enhance user comfort. Furthermore, the wool fibers may be used by ammonia decomposition so that smell may be avoided or reduced.

The kapok fibers are particularly advantageous as no preparation may is required before they are used in a dry forming process for forming the liquid impermeable back side layer. In order to make the layer as tight as possible, only the previously mentioned heat compacting of the fibers is required.

Alternatively, however, it is possible to use binders of polyethylene, polypropylene, polyester fibers or bicomponent fibers. Hereby, a heat compacting may be performed, and simultaneously there is created a very tight outermost surface layer in the top layer when temperatures between 145° C. to 156° C. are applied, depending on the production speed of the machine. The compacting occurs with a very high pressure so that a completely sealing liquid barrier layer is formed.

Even though the fibers may be coherent due to their fibrillation, it is possible to use binders. As binding means traditional latex binders may be used. However, it is possible that eveanyl acetate binders may be used instead for avoiding detrimental effects for the user, or binders made from potato, rice, or corn starch.

It is to be noted that in the above description we are generally speaking about hydrophobic vegetable fibers. With vegetable fibers is meant fibers coming from nature, irrespectively whether these fibers come from trees, bushes or plants. Thus, some kapok fibers will come from trees. The animal fibers are indicated as wool fibers and may come from sheep or other animals from which it is suitable to utilize the wool fibers.

What is claimed is:

1. An absorbing article having a hydrophobic, liquid permeable top layer, a hydrophobic liquid impermeable back side layer and a hydrophilic core layer, the improvement comprising that at least the back side layer comprises hydrophobic vegetable fibers or animal fibers.

2. An absorbing article according to claim 1 wherein the hydrophobic vegetable fibers comprise kapok fibers.

3. An absorbing article according to claim 1, wherein all the hydrophobic layers comprise hydrophobic vegetable fibers.

4. An absorbing article according to claim 1, wherein at least the top layer comprises wool fibers.

5. An absorbing article according to claim 1, wherein the absorbing layer comprises absorbents in the form of vegetable starch material, and that the absorbents are fixed in an open structure of vegetable and/or wool fibers.

6. An absorbing article according to claim 1, wherein all three layers are made by a dry forming process.

7. An absorbing article according to claim 1, wherein an outermost surface layer of the back side layer is impregnated with a liquid barrier agent.

8. An absorbing article according to claim 1, wherein the back side layer is made by heat compacting.

9. An absorbing article according to claim 1, wherein an outermost surface layer of the top layer is impregnated with a liquid barrier agent.

10. An absorbing article according to claim 1, wherein the top layer is provided with mechanically formed holes for passage of liquid through the layer.

11. An absorbing article according to claim 5, wherein the vegetable starch material is potato flour.

12. An absorbing article according to claim 7, wherein the liquid barrier agent is glycerine.

13. An absorbing article according to claim 9, wherein the liquid barrier agent is glycerine.

* * * * *